(12) United States Patent
Schwendeman et al.

(10) Patent No.: US 8,017,155 B2
(45) Date of Patent: Sep. 13, 2011

(54) METHODS FOR ENCAPSULATION OF BIOMACROMOLECULES IN POLYMERS

(75) Inventors: Steven P. Schwendeman, Ann Arbor, MI (US); Samuel E. Reinhold, III, Ann Arbor, MI (US); Jichao Kang, Pennington, NJ (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1104 days.

(21) Appl. No.: 11/596,524

(22) PCT Filed: May 16, 2005

(86) PCT No.: PCT/US2005/017140
§ 371 (c)(1),
(2), (4) Date: May 29, 2007

(87) PCT Pub. No.: WO2005/117942
PCT Pub. Date: Dec. 15, 2005

(65) Prior Publication Data
US 2008/0131478 A1    Jun. 5, 2008

Related U.S. Application Data

(60) Provisional application No. 60/571,029, filed on May 14, 2004.

(51) Int. Cl.
*A61K 9/52* (2006.01)
*C07K 14/00* (2006.01)

(52) U.S. Cl. .............................. 424/490; 536/23.1; 514/2

(58) Field of Classification Search .................. None
See application file for complete search history.

(56) References Cited

U.S. PATENT DOCUMENTS 5,470,582 A * 11/1995 Supersaxo et al. ............ 424/489
6,962,716 B1 * 11/2005 King et al. ..................... 424/489

* cited by examiner

*Primary Examiner* — Anand Desai
(74) *Attorney, Agent, or Firm* — Harness, Dickey & Pierce, P.L.C.

(57) ABSTRACT

A method for encapsulating a biomacromolecule in a pore-containing polymer comprising the steps of providing an encapsulating solution containing the biomacromolecule and the pore-containing polymer; contacting the biomacromolecule with the pore-containing polymer for a time sufficient for the biomacromolecule to enter the pores of the pore-containing polymer; and rearranging the polymer such that the surface pores of the polymer are closed thus encapsulating the biomacromolecule in the pore-containing polymer.

18 Claims, 4 Drawing Sheets

METHODS FOR ENCAPSULATION OF BIOMACROMOLECULES IN POLYMERS

CROSS-REFERENCE TO RELATED APPLICATIONS

This application claims priority to U.S. Provisional Patent Application No. 60/571,029 filed May 14, 2004, the entirety of which is incorporated herein by reference.

STATEMENT ON FEDERALLY FUNDED RESEARCH

This invention was funded, at least in part by National Institutes of Health grant number HL 68345. The government may have certain rights in this invention.

BACKGROUND OF THE INVENTION

Injectable biodegradable polymeric particles (usually microspheres) represent an exciting approach to control the release of vaccine antigens to reduce the number of doses in the immunization schedule and optimize the desired immune response via selective targeting of antigen to antigen presenting cells. After the first couple of decades of their study, much progress has been made towards the clinical use of antigen-loaded microspheres. Poly(lactide-co-glycolic acids) (PLGAs) have been studied most commonly for this purpose because of their proven safety record and established use in marketed products for controlled delivery of several peptide drugs. PLGA microspheres have many desirable features relative to standard aluminum-based adjuvants, including the microspheres' ability to induce cell-mediated immunity, a necessary requirement for emergent vaccines against HIV and cancer. PLGA microparticles have displayed unprecedented versatility and safety to accomplish release of one or multiple antigens of varying physical-chemical characteristics and immunologic requirements, and have now met numerous critical benchmarks in development of long-lasting immunity after a single injected dose.

Chances are that for every important protein that has undergone pharmaceutical development, the polymer-controlled release option, at the very least, has been considered seriously and, in many cases, aggressively pursued. Unfortunately, successful controlled release of proteins has been a daunting task and, until recently, there has been significant doubt whether a significant number of therapeutic proteins could be slowly and completely released in a native state from the biodegradable polymer-of-choice for general biomedical applications, copolymers from lactic and glycolic acids. Thus, the most significant obstacle in the development of controlled-release injectable depots for proteins has emerged as the instability of the protein during encapsulation and release in vivo.

Hydrophilic macromolecules, like proteins, cannot diffuse through the hydrophobic polymer phase, like through PLGA. The release of encapsulated protein drugs from PLGA requires at some point the diffusion of the macromolecules through water-filled pores and channels. Protein release from PLGA microspheres typically follows a tri-phasic behavior. First, protein on the surface or having access to the surface of microspheres (i.e., in open pores) is released rapidly, which is the source of the initial burst release. Then, there is a lag time because protein cannot diffuse through the polymer phase. The continuous protein release will not occur until polymer erosion begins, which will produce more pores and channels and consequently let protein in previously isolated pores release out.

Most theoretical frameworks to date regarding protein release have neglected the dynamics of polymer microstructure; namely the kinetics of pore opening and closing.

Current methods for encapsulating molecules, such as biomacromolecules in biodegradable polymers involves harsh processing conditions, such as organic solvents, excess heat, mixing and so forth, which can denature and/or destabilize proteins and other biomacromolecules. Additionally, drying and micronization of biomacromolecules, which often occurs prior to encapsulations may further destabilize the biomacromolecules.

Accordingly, a need exists for new methods of encapsulating biomacromolecules in pore-containing polymers, such as PLGA. The method should be able to be performed without need for organic solvent or other harsh processing conditions during encapsulation, which can denature proteins or destabilize other biomacromolecules. There should also be no need for micronization of the protein or poly(nucleic acid) before encapsulation, which can destabilize both biomacromolecules. A need exists for a method of encapsulation wherein there is no need for drying of the biomacromolecule, which can also destabilize this species.

A need further exists for a method wherein the polymer microspheres could be acceptably terminally sterilized (e.g., by gamma irradiation) before encapsulation with small losses in polymer molecular weight, wherein the sterile protein (or biomacromolecule)-containing solution and sterile microspheres could be placed in a syringe and microencapsulation could be performed at the point-of-care, or sterile protein solution could be added to sterile microspheres as typically done with a diluent being added to typical dry microspheres that already contain protein.

There also exists a need for new methods of encapsulation which are less expensive to carry out than conventional methods, which may be a principal factor in the slow development of more controlled release injectable depots. Furthermore the new method should be applicable to tissue engineering scaffolds, presumably, and any type of biomaterial (or any other polymer encapsulation system, e.g., agricultural) that requires the need to encapsulate molecules that do not strongly partition into the polymer phase, but in pores (typically aqueous as in biomaterials) of the polymer.

SUMMARY OF THE INVENTION

Provided herein are methods for encapsulating a biomacromolecule in a pore-containing polymer comprising the steps of providing an encapsulating solution containing the biomacromolecule and the pore-containing polymer; contacting the biomacromolecule with the pore-containing polymer for a time sufficient for the biomacromolecule to enter the pores of the pore-containing polymer; and closing the pores of the pore-containing polymer wherein the biomacromolecules is encapsulated in the pore-containing polymer.

In various embodiments of the methods described herein, the biomacromolecule may be proteins, peptides, poly(nucleic acid) drugs, antigens, and so forth, and combinations thereof.

In accordance with the methods provided herein, the biomacromolecules of interest may be encapsulated in biodegradable polymers which have already been formed into microspheres, tissue engineering scaffold, or other usable form prior to encapsulating the biomacromolecule. Accordingly, in some embodiments, the pore-containing polymer is a preformed microsphere. In other embodiments, the pore-containing polymer is a preformed tissue engineering scaffold.

In some embodiment, the pore-containing polymer is poly (DL-lactide-co-glycolide) (PLGA). In other embodiments, other pore-containing biodegradable polymers may also be used.

In accordance with the methods provided herein, the pores of the biodegradable polymer may be closed by changing the temperature of the encapsulating solution once the biomacromolecules have entered the pores of the polymer by any one or more of several different polymer rearrangements. In some embodiments, the pores are closed by changing the temperature of the encapsulating solution. In some embodiments, the pores are closed, at least in part by changing the pH of the encapsulating solution. In some embodiments, the pores are closed, at least in part by using of pore-closing additives in the pore-containing polymer. In some embodiments, the pores are closed, at least in part by using of pore-closing additives in the encapsulation solution. And in still other embodiments, more than one of these polymer rearrangement mechanisms are used to close the pores in the pore-containing polymer once the biomacromolecules have entered the pores.

DETAILED DESCRIPTION OF THE INVENTION

Figure 1:
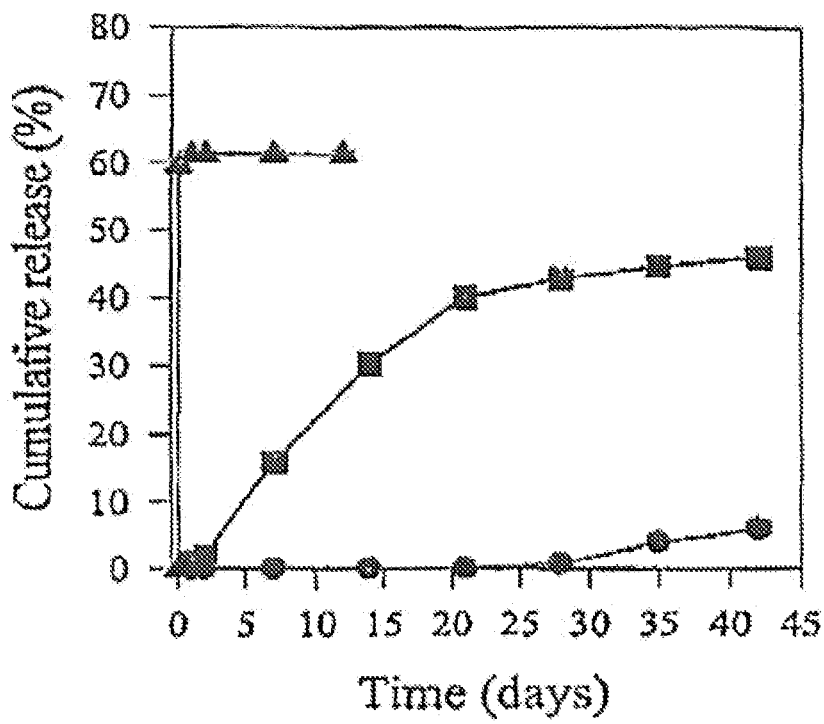
FIG. 1. Cumulative BSA release from PLGA microspheres of formulations A (▲), B (●) and C (■). (Average±S.T.D., n=3)

Provided herein are methods of encapsulating molecules of interest, such as biomacromolecules, including proteins, peptides, poly(nucleic acids) drugs, vaccine antigens, and so forth in pore-containing polymers. The methods generally involve placing a solution containing the biomacromolecule in contact with a polymer containing pores, or a solution containing the biomacromolecule in contact with a polymer, allowing the biomacromolecule to enter the pores, and then causing the pores to close, wherein the biomacromolecule is entrapped, encapsulated, or irreversibly absorbed in the polymer. In accordance with the methods provided herein, the pore-containing polymer is not soluble in the encapsulation solution nor is the polymer dissolved during encapsulation. The pore-containing polymer may be plasticized, however.

Macromolecules such as peptides, proteins, poly(nucleic acid) drugs and vaccine antigens can be encapsulated in already prepared poly(lactic-co-glycolic acid) PLGA (or other polymeric biomaterial) microspheres or tissue engineering scaffolds by simple mixing of the microspheres/scaffolds in aqueous solutions containing the desired macromolecule followed by polymer rearrangements that cause pores to close. Temperature, pH, and additives (either in already prepared microspheres or in encapsulating solution) can be used to manipulate polymer pore closing. For example, PLGA pores remain largely open at 4° C. whereas rapidly close at 37° C. Also lower pH in encapsulation solution (contain macromolecule) and adding glucose in the already-prepared microspheres appears to accelerate pore closing.

The methods described herein are particularly useful for encapsulation of biomacromolecules in biodegradable polymers. There is no need for organic solvent or other harsh processing conditions during encapsulation, which can denature proteins or destabilize other biomacromolecules. There is no need for micronization of the protein or poly(nucleic acid) before encapsulation, which can destabilize both biomacromolecules.

The pore-containing polymers used in the methods described herein may be poly(lactide-co-glycolic acids) (PLGAs) and related copolymers, including any polymer containing a polyester with lactic and/or glycolic acid repeat units. The polymers may be made by any method, and may be linear, star, branched, cross-linked, or any configuration so long as the polymer has lactic and/or glycolic repeat units, which may be liberated by hydrolysis. In accordance with the methods described herein, the pore-containing polymers may be preformed prior to the encapsulation step, i.e., the microspheres or tissue engineering scaffold may be formed according to known methods prior to contacting the biomacromolecules to be encapsulated.

Additionally, before encapsulation, the polymer microspheres could be acceptably terminally sterilized (e.g., by gamma irradiation) with small losses in polymer molecular weight. The sterile protein (or biomacromolecule)-containing solution and sterile microspheres could be placed in a syringe and microencapsulation could be performed at the point-of-care, or sterile protein solution could be added to sterile microspheres as typically done with a diluent being added to typical dry microspheres that already contain protein. Furthermore, when encapsulation is performed at time of administration or shortly thereafter, there is no need for drying of the biomacromolecule, which can also destabilize this species.

Additionally, the normal concept of reducing acidic impurities in the polymer may be reversed. Typically impurities are removed in order to minimize initial burst and improve polymer stability, whereas some impurity may facilitate the pore closing by plasticizing the polymer. Therefore, there may be a reduced need for achieving low levels of typical acid impurities following polymerization of the PLGA, for example.

Even more advantageously, during microsphere formation, the polymer could be subjected to numerous stresses (excess heat, mixing, etc.) that normally cannot be used because a peptide/protein/DNA are present, which will not survive. In addition, certain elements during microsphere processing may be very difficult to conduct under aseptic processing, which now would not be excluded because terminal sterilization could be performed. Therefore, the element of control over the ultimate microsphere morphology and the kind of microsphere (scaffold) prepared is vastly increased if encapsulation is performed after microsphere (scaffold) preparation.

This method is expected to be much less expensive to carry out, which may be a principal factor in the slow development of more controlled release injectable drugs.

The methods provided herein are also applicable to tissue engineering scaffolds, as well as any type of biomaterial (or any other polymer encapsulation system, e.g., agricultural) that requires the need to encapsulate molecules that do not strongly partition into the polymer phase, but in pores (typically aqueous as in biomaterials) of the polymer.

In accordance with methods described herein, a biomacromolecule solution is placed in contact with a polymer containing pores, or one that develops pores when in contact with the solution. At the same time or after some soaking period the polymer experiences conditions that cause spontaneous polymer chain rearrangements, which in turn cause the accessible pores (pores having access to the polymer surface) to close. When these pores close the biomacromolecule becomes entrapped, encapsulated, or irreversibly absorbed.

In most embodiments, the encapsulation efficiency (weight biomacromolecule encapsulated/weight biomacromolecule in solution exposed to polymer) using the inventive methods is greater than 10%. In some embodiments, the encapsulation efficiency is greater than 15%. In some embodiments, the encapsulation efficiency is greater than 20%. In some embodiments, the encapsulation efficiency is greater than 25%. In some embodiments, the encapsulation efficiency is greater than 30%. In some embodiments, the encapsulation efficiency is greater than 35%. In some embodiments, the encapsulation efficiency is greater than 40%. In some embodiments, the encapsulation efficiency is greater than 45%. In still other embodiments, the encapsulation efficiency is greater than 50%.

The biomacromolecules may be any biomacromolecule of interest. The methods provided herein are particularly useful for biomacromolecules that would be subject to degradation when exposed to conditions used in preparing pore-containing microspheres. Some non-limiting examples of possible proteins that may be used with the inventive methods include, but are not limited to, the biomacromolecules may be such things as bovine serum albumen, hen egg-white lysosome, ribonuclease A, growth hormone, tetanus toxoid, erythropoietin, insulin-like growth factor-I, vascular endothelial growth factor, bone morphogenetic protein, and basic fibroblast growth factor.

Experimental Section

Materials Poly(DL-lactide-co-glycolide) 50/50, end-group capped, with an inherent viscosity of 0.17 d.l/g in HFIP at 30° C. was obtained from Birmingham polymers, Inc, (Birmingham, Ala.). Poly(DL-lactide-co-glycolide)-Glucose (50/50, with a MW of 50 kDa) was a generous gift from Novartis Pharm AG (Basle, Switzerland). Poly(vinyl alcohol) (PVA) (80% hydrolyzed, MW 9-10 kDa) was from Aldrich Chemical Company, Inc. (Milwaukee, Wis.). Bovine serum albumin (BSA), magnesium carbonate and FITC-Dextran (MW=70 kDa) were from Sigma Chemical Company (Louis, Mo.). 7-methoxy-coumarin-3-carbonyl-azide, dextran-bodipy (Mw=10,000) and BSA-bodipy were from molecular probes (Eugene, Oreg.). Dextran, with Mw=10,000 was from Polysciences, Inc. (Warrington, Pa.). Dextran-bodipy, which has a MW of 10 kDa, as well as FITC-dextran (70 kDa) were dialyzed extensively before use. All other reagents were analytical grade or higher and used as received.

Labeling Dextran with Coumarin—a pH Insensitive Fluorescent Probe pH-insensitive fluorescence probe, coumarin, was conjugated to dextran. Briefly, 100 mg dextran was dissolved in 4 ml DMSO together with 4 mg of 7-methoxy-coumarin-3-carbonyl-azide. The mixture was put into a 70° C. oven for 3 h. 12 mL of water was added to the reaction mixture after it cool down to room temperature. Then the mixture was put into a −20° C. freezer for 30 min. The un-reacted free probe and DMSO was removed by filtration and extensive dialysis using a Spectra/Pro® membrane with a MWCO of 1,000 (Spectrum laboratory, Inc., Rancho Dominguez, Calif.). Finally, the dextran-coumarin conjugate was lyophilized and stored at −20° C. for future use. The labeling rate was calculated by fluorescent intensity of the conjugated dextran.

Encapsulation of BSA in Microspheres by W/O/W Double Emulsion-Solvent Evaporation Microencapsulation Method PLGA microspheres were prepared by adding 100-200 µl of 300 mg/ml BSA in PBS (8 mM $Na_2HPO_4$, 2 mM $KH_2PO_4$, 137 mM NaCl, 3 mM KCl, pH 7.4) solution to 1 ml of 700 mg/ml PLGA in $CH_2Cl_2$ solution. The mixture was homogenized at 10,000 rpm with a Tempest $IQ^2$® homogenizer (The VirTis Company, Gardiner, N.Y.) equipped with a 10 mm shaft in an ice/water bath for 1 min to make the first emulsion. Two mL of 5% PVA (9-10 k, 80% hydrolyzed) solution was immediately added to the first emulsion and the mixture was vortexed (Genie 2, Fisher Scientific Industries, Inc., Bohemia, N.Y.) for 15 s to make the w/o/w emulsion. The resultant emulsion was poured to 100 ml of 0.5% PVA solution under stirring condition. The microspheres were hardened at room temperature for 3 h under continuous stirring. Hardened microspheres were collected by centrifugation, washed three times with purified water, and finally freeze-dried. For freeze-drying, samples were flash frozen in liquid nitrogen and placed on a Freezone® 6 freeze-drying system (Labcono, Kansas City, Mo.) at $133 \times 10^{-3}$ mbar or less vacuum at a condenser temperature of −46° C. for 48 h. 3% $MgCO_3$ was suspended in polymer solution when base-containing PLGA microspheres were prepared.

To observe the protein distribution in PLGA microspheres, PLGA microspheres encapsulating BSA-bodipy spiked BSA was also prepared by w/o/w emulsion-solvent evaporation method.

PLGA-glucose microspheres encapsulating both BSA and dextran-FITC (MW T 70,000) were also prepared using the above-described method. 300 mg/mL PLGA-Glu in CH.sub.2C1.sub.2 was used in this preparation. The internal phase consisted of 200 mg/mL BSA and 18 mg/mL dextran-FITC. After hardening, the microspheres were collected into two parts by sieving, one part is between 20 and 45.mu.m and the other is between 45 and 90.mu.m. All other procedures and condition were the same as for the PLGA microspheres.

Morphology Characterization and Size Distribution of Microspheres by Scanning Electron Microscopy Microspheres were first coated with gold for 200 s by a Vacuum Coater (Desk II, Denton Vacuum, Inc, Hill, N.J.). Microsphere morphology was then observed by a scanning electron microscope (S3200N variable pressure SEM, Hitachi) with a voltage of 15 keV. For size distribution analysis, the sizes of more than 200 particles were measured from SEM micrographs. For observation of cross-section, microspheres were cut by a razor blade in a glass slide before coating.

Measurement of Protein and Dextran-FITC Concentration

Protein concentration was determined either by a Coomassie Plus (Pierce, Rockford, Ill.) protein assay or by a size exclusion chromatography, For the size exclusion chromatography, a TSK 2000 SWxI (Toso Biosep LLC, Montgomeryville, Pa.) column with a guard cartridge was used. The mobile phase consisted of 50 mM sodium phosphate and 150 mM sodium chloride and was delivered at 1 ml/min by a Waters (Milford, Mass.) 1525 pump. A Waters 2487 dual wavelength detector was used to monitor the elution at 280 mn.

The concentration of dextran-FITC was determined by a FluoroMax-2® fluorometer (Instruments S.A., Edison, N.J.) at λex=495 nm and λem=515 nm against a standard curve, which has a $R^2$ of 0.9996.

Protein and Dextran Loading in Microspheres

The loading of protein and dextran in microspheres was determined by reconstitution of protein and dextran in water after removing the polymer by acetone. The encapsulation efficiency was calculated as the ratio of the actual loading to the theoretical loading.

Evaluation of Protein and Dextran Release from Microspheres

In Vitro release studies were carried out under mild agitation conditions. 10-15 mg of microspheres were placed in 1.5 ml microcentrifuge tubes with 1 ml PBST (PBS, pH 7.4 with 0.02% Tween-80) and incubated at 4, 25, 37 or 45° C. At pre-determined time intervals, release medium was replaced. The concentration of protein and dextran in the release medium was then measured to calculate the cumulative release of protein and dextran from microspheres.

Dextran Uptake by Laser Scanning Confocal Microscopy

Dextran uptake was monitored by LSCM following the incubation of microspheres in dextran-probe solution.

100 µl of either 2.5 mg/ml dextran-bodipy (MW=10,000) or 20 mg dextran-coumarin (MW=10,000) in PBST was added to about 5 mg microspheres with or without pre-incubation. After incubation at 4° C. or 37° C. for 5 h or 12 h, probe-conjugated dextran was removed. Microspheres were then washed twice before observation of the dextran-probe distribution by laser LSCM.

A Carl Zeiss LSM 510 (Car Zeiss Microimaging, Inc, Thornwood, N.Y.) laser scanning confocal microscope was used to observe the probe distribution in microparticles. The instrument was equipped with four laser systems, an Ar laser (458, 488, 514 nm, 25 mW), a HeNe 1 laser (543 nm, 1 mW), a HeNe laser 2 (633 nm) and an Enterprise laser (351, 364 nm, 80 mW), a photomultiplier (PMT) and a computer for image building and instrument control. The connected microscope was a Carl Zeiss inverted Axiovert 100 M that was fully motorized and could be operated via the LSM 510 software. A C-Apochromat 63×N.A. 1.2 water immersion objective lens was used to build images. The pinhole was set at 150 p.m. The laser was focused in the center of a microsphere and a 1024×1024 pixels image was scanned at a scan speed of 1.60 µs/pixel. The 488 nm line of the Ar-ion laser and LP 505 filter was used for dextran-bodipy, laser was set at 5% of 25 mW (1.25 mW). For dextran-coumarin, the 364 nm of the Enterprise laser and a BP 485-470 filter was used. The laser was set at 2.5% of 80 mW (2 mW).

Curve Fitting and Diffusion Coefficient Calculation

Because of low loading and high solubility, protein/dextran release could be regarded as drug release from a monolithic solution. The release medium was also frequently changed to guarantee the sink conditions. Crank's solution for the release from spherical geometry under these conditions is as follows:

$$\frac{M_t}{M_\infty} = 1 - \frac{6}{\pi^2}\sum_{nwl}^{\infty}\frac{1}{n^2}\exp(-D_{eff}n^2 t/a^2$$

where t is time and $D_{eff}$ is the effective diffusion coefficient in the polymer matrix. $M_t$ and $M_n$ are the released drug amount at time t and the releasable drug amount at infinite time, respectively. The fitting was carried out according to a least-square nonlinear regression using n=12 (DataFit®, Oakdale engineering, Oakdale, Pa.) to obtain the values of $D_{eff}$. Using values larger than n=12 did not change the fitted value of $D_{eff}$.

Results

Effect of Formulation Variables on Protein Release from PLGA Microspheres

We prepared both regular PLGA microspheres and PLGA-Glu microspheres by double-emulsion solvent-evaporation method. In the case of PLGA-Glu microspheres, both BSA and dextran-FITC were encapsulated in microspheres. The BSA loading in 20-45 gm and 45-90 gm fractions were 3.9±1.3% and 3.7±1.2%, respectively, with a encapsulation efficiency of 62%. The dextran-FITC loading in 20-45 gm and 45-90 pm fractions were 0.44±0.002% and 0.43±0.005%, respectively, with a encapsulation efficiency of 77%. It was shown by scanning electron microscopy that the PLGA-Glu microspheres were porous both in the surface and inside.

Although the size of microspheres were different between microspheres with a size of 20-45 µm and of 45-90 µm, both BSA and dextran loading in these microspheres were essentially the same, which indicated that the distribution of protein in different size of microspheres made by double emulsion were rather uniform. There was no size-dependent distribution of the encapsulated macromolecules. The other interesting finding was that dextran-FITC had slightly higher microencapsulation efficiency than BSA. This indicated that the interaction between polymer and protein on encapsulation efficiency was only minimum. Since dextran should have smaller interaction with the polymer than BSA, we would expect lower encapsulation efficiency for dextran than for BSA if the polymer-protein interaction were the determining factor for encapsulation efficiency. Because we encapsulated both BSA and dextran in the same microspheres, the effect of tensoactive properties of protein or emulsion formation on encapsulation efficiency was excluded. The slightly higher encapsulation efficiency of dextran than BSA could be attributed to the higher MW of dextran (70 KDa over 67 KDa) and linear molecular structure.

As seen in Table 1, by maneuvering the volume of internal phase, adding anti-acidic insoluble base, and adding salt in hardening buffer we obtained three microspheres with distinct properties. Microspheres A have a protein loading of 4.4±0.1% and a high initial 1-day release of 61.3±0.5%. Burst release was eliminated by adding 5×PBS in the hardening buffer in microspheres B and C. 3% MgCO$_3$ was added to microsphere C to neutralize the acidic microenvironment in PLGA microspheres caused by acidic PLGA degradation species. It was found that microsphere A, which had a bigger burst release, had a relative porous surface and interior. Microspheres B and C, with very limited burst release, had relative dense surface and interiors.

FIG. 1 shows the distinct release profiles of PLGA microspheres A, B and C. Formulation A released 61% BSA in the first 2 h followed by a no release in the first 2 weeks of incubation at 37° C. On the contrary, formulation B and C, had a minimum initial burst. Formulation B had no release until 4 weeks while formulation C had a continuous release throughout the 5 weeks of incubation at 37° C.

TABLE 1

Effect of formulation variables on protein release from PLGA microspheres

| Formulation | Internal phase ratio (%) | Base content (%) | Hardening buffer | Protein loading (%) | Encapsulation efficiency (%) | 1st day release (%) |
|---|---|---|---|---|---|---|
| A | 1/5 | 0 | 0.5% PVA | 4.4 ± 0.1 | 67 | 61.3 ± 0.5 |
| B | 1/10 | 0 | 0.5% PVA + 5 × PBS | 37 ± 0.2 | 90 | 0.1 ± 0.1 |
| C | 1/5 | 3 | 0.5% PVA + 5 × PBS | 6.6 ± 0.1 | 82 | 1.4 ± 0 |

Dependence of Protein Release from PLGA-Glucose Microspheres on Temperature

Figure 2:
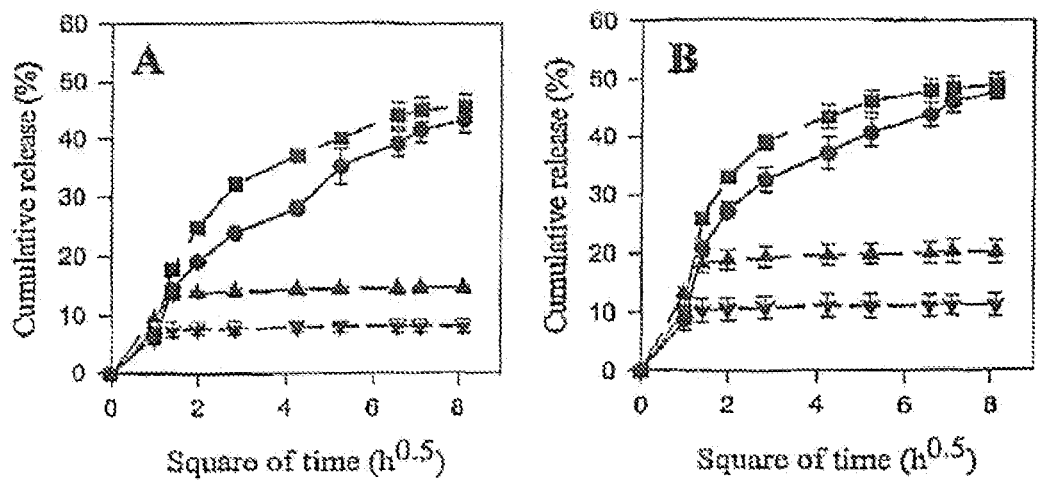
FIG. 2. BSA (A) and dextran (B) release from PLGA-Glu microspheres at 4 (▼), 25 (▲), 37 (■)and 45 (■) ° C. (Average*S.T.D., n=3)

PLGA-Glu microspheres, having a size of 45-90 urn and containing both BSA and dextran, were incubated in PBST at 4, 25, 37 and 45° C. The release of both BSA and dextran was measured for 3 days. As shown in FIG. 2A, BSA release at 37° C. followed a typical protein release profile. 18% BSA was released in the first 2 hours, which was followed by only minimum release, At 45° C., BSA release followed a similar profile; only 10% protein was released. On the contrary, BSA release at 4° C. and 25° C. degree followed a continuous release profile. 21% and 26% BSA was released at the first 2 h from microspheres incubated at 4° C. and 25° C., respectively. By 66 h, the cumulative BSA release from microspheres incubated at 4° C. and 25° C. reached 48% and 49%, respectively. As shown in FIG. 2B, dextran release showed similar temperature-dependent pattern with a slightly slower rate. The cumulative release after 66 h at 4, 25, 37 and 45° C. were 43, 46, 15 and 8%, respectively. Because higher temperature is accompanied with higher diffusivity, we would expect opposite results if the microspheres structure and polymer properties remained same during the release period. The faster protein release at 4 and 25° C. than at 37 and 45° C. could not be attributed to polymer degradation either, because higher temperature would result in faster polymer degradation. Before incubation, significant amount of protein was accessible to the microsphere surface, which was the prerequisite to the protein release. At 4° C. and 25° C., the polymer structure remained essentially intact, so the protein could be released continuously by Fickian diffusion. However, at higher temperatures, i.e. 37° C. and 45° C., the pores and channels that used to open to the surface were somehow closed, so the protein release was suddenly stopped.

Figure 3:
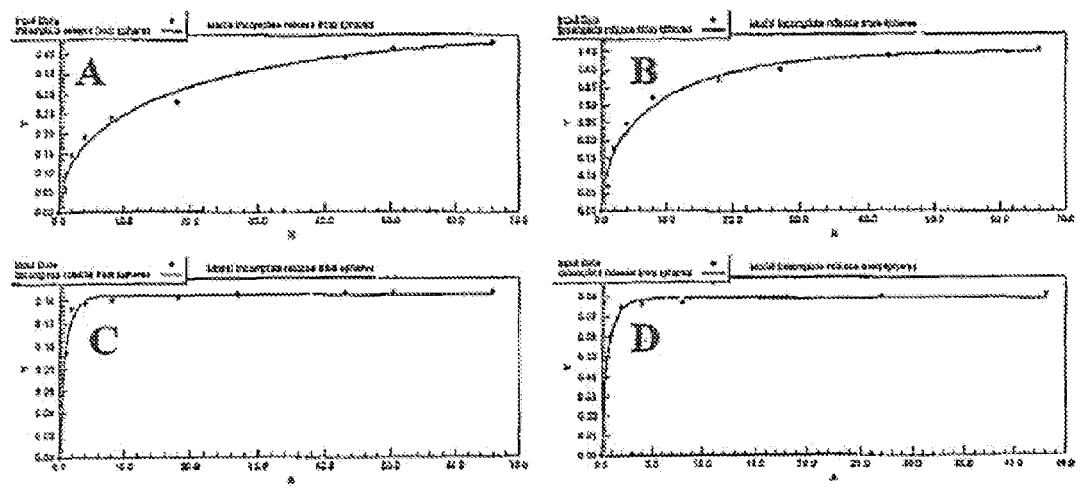
FIG. 3. Dextran release (symbol) from PLGA-Glu microspheres at 4 (A), 25 (B), 37 (C) and 45 (D) ° C. and their fitting curves (lines)
Figure 4:
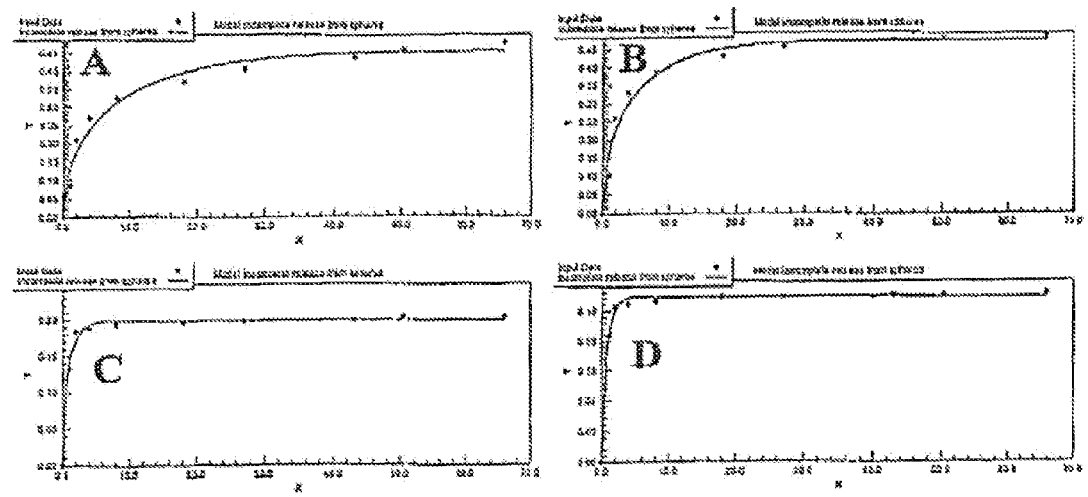
FIG. 4. BSA release (symbol) from PLGA-Glu microspheres at 4 (A), 25 (B), 37 (C) and 45 (D) ° C. and their fitting curves (lines)

Crank's solution for drug release from spherical geometry under sink condition was fitted to the release of both BSA and dextran at investigated temperatures. The results are shown in FIGS. 3 and 4 and Table 2. As seen in FIGS. 3 and 4, both BSA and dextran release can be explained by the Crank's solution for solute release from spherical geometry under sink condition with a limited releasable fraction. The limited releasable fraction could be explained by the hypothesis that only limited fraction of encapsulated macromolecules had access to the surface of microspheres and thus releasable. The releasable fraction of macromolecules at 4° C. and 25° C. was comparable, indicating the pore/channels state remained same when the microspheres were incubated between 4° C. and 25° C. The faster release rate of macromolecules at 25° C. than at 4° C., reflected by the bigger diffusion coefficient, can be explained by the effect of temperature on the diffusion coefficient of macromolecules. As shown in Table 2, the calculated diffusion coefficient of dextran at 25° C. which is simulated from the Frank's solution is the same as the value of diffusion coefficient calculated by Einstein-Stokes equation.

However, the releasable fraction of macromolecules decreased significantly at 37° C. and 45° C. Releasable fraction of BSA decreased from 45% to 20% at 37° C. and to 11% at 45° C., indicating more pores were closed at higher temperature. Dextran exhibited a similar trend.

TABLE 2

Fitted and calculated parameters of macromolecular release from PLGA-Glu

| | | Temperature (° C.) | | | |
|---|---|---|---|---|---|
| | | 4 | 25 | 37 | 45 |
| $D (\times 10^{-11} cm^2/s)$ | BSA | 2.6 | 4.1 | 22 | 30 |
| | Dextran-70K | 1.1 | 2.2 | 24 | 31 |
| | Dextran-70K Calculated* | 1.1 | 2.2 | 2.9 | 3.5 |
| Releasable fraction (%) | BSA | 45 | 48 | 20 | 11 |
| | Dextran-70K | 45 | 45 | 15 | 8 |

*Calculated using Einstein-stokes equation assuming D at 4° C. is $1.1 \times 10^{-11}$ cm$^2$/s.

Dependence of Pore State in PLGA-Glu Microspheres on Temperature

It was noted that before incubation, PLGA-Glu microspheres have a porous surface and interior. After 2 days of incubation at 4° C., microspheres remained porous both on surface and interior, which was confirmed by scanning electron microscopy (data not shown). However, incubation at 37° C. altered the microsphere morphology significantly. Most of the pores on surface disappeared after 2 hrs of incubation at 37° C. Continuous incubation at 37° C. for 2 days only had minimal effect on microsphere morphology. The interior of PLGA-Glu microspheres didn't change significantly when incubated at 37° C. in contrast to the change on surface. This is the visual evidence for the hypothesis that pores on PLGA-Glu surface close quickly when incubated at 37° C. or higher temperature, but not at 4° C.

Dextran uptake was also used to characterize the pore state in PLGA-Glu microspheres. Dextran (MW=10 kDa) was first labeled with pH insensitive dye, coumarin. The labeling rate is 0.1% of coumarin per glucose unit. The low labeling rate would assure the conjugation of probe molecules would not affect the hydrophilic nature of dextran. The uptake of dextrancoumarin was observed by L SCM. Higher uptake rate represents a combination of higher porosity and pore connectivity, which is directly correlated with protein release from microspheres because uptake of dextran is essentially a reverse process of protein release. Because the observation was carried out at wet state, the potential alteration of microsphere morphology by drying of microspheres was also avoided. Confocal microscopy showed the 12 h uptake of dextran-coumarin by PLGA-Glu microspheres with or without pre-incubation at 4° C. and 37° C. (data not shown). Microspheres were washed with PBST briefly and immediately observed by LSCM. Because only small amount of dextran-coumarin was absorbed by microspheres, the uptake can't be observed without washing away the dye solution in surrounding environment, which imposed a very bright background. The uptake of dextran-coumarin decreased significantly after the microspheres were pre-incubated at 37° C. for 2 days, which corresponded to the pore closing on the surface of PLGA-Glu observed by SEM (data not shown).

Dextran Uptake by PLGA Microspheres with High Burst Release

PLGA microspheres (preparation A) exhibited the same phenomenon when incubated at different temperatures. It was observed that incubation at 4° C. for 2 days didn't change the microsphere morphology. On the other hand, 2 h of incubation at 37° C. significantly changed the pore state. All pores on microsphere surface were either closed completely or to the size that is out of the distinction power of SEM. The dextran uptake by PLGA microspheres demonstrated a dramatic effect of incubation on pore state in microspheres. It was observed that PLGA microspheres without pre-incubation absorbed significant amount of dextran-bodipy (MW=10 kDa) (data not shown). The bright spots in the microspheres were the absorbed dextran-bodipy. This indicated that although there were only limited pores on the surface of PLGA microspheres, as observed by SEM (not shown), the pores inside microspheres had access to the surrounding environment through other pores/channels. The big dextran uptake is corresponding to the big initial release rate of protein from PLGA microspheres (preparation A). Pre-incubation at 4° C. didn't affect the dextran-uptake capability of PLGA microspheres, indicative of the unaltered pore state. However, as in the case of PLGA-Glu microspheres, pre-incubation at 37° C. significantly changed the pore state of PLGA microspheres. It was observed that only minimum dextran-uptake could be observed by LSCM when the microspheres were pre-incubated at 37° C. for 2 h, which was in accordance with the no release phenomenon after the initial burst for this PLGA microspheres, as shown in FIG. 1, preparation A. After dextran uptake, microspheres were incubated in blank PEST at same temperature, i.e., 4° C. or 37° C. for 24 h and then observed for the dextran-bodipy distribution in the microspheres. As we expected for the microspheres without pre-incubation, almost all the dextran stayed in the microspheres after incubation with blank medium for 24 hr at 37° C. This was because the pores were closed during incubation with blank medium at 37° C. Previous open pores became isolated pores; thus the previously absorbed dextran-bodipy was trapped in the microspheres. For microspheres incubated at 4° C., if the pore state remained exactly the same during incubation, we would expect that all the previously absorbed dextran-bodipy would diffuse out to the surrounding medium and essentially no dextran would be left in the microspheres since the volume of surrounding medium was much bigger than microspheres. It turned out that although some previously absorbed dextran was indeed released, there was still substantial amount of dextran trapped in microspheres after incubation in blank medium. This observation suggested that at least some of the pores lost their access to the surrounding environment even when incubated at 4° C. for 12 h, so that some dextran was trapped in PLGA microspheres.

Effect of Neutralizing Insoluble Base on Pore State in PLGA Microspheres

Figure 5:
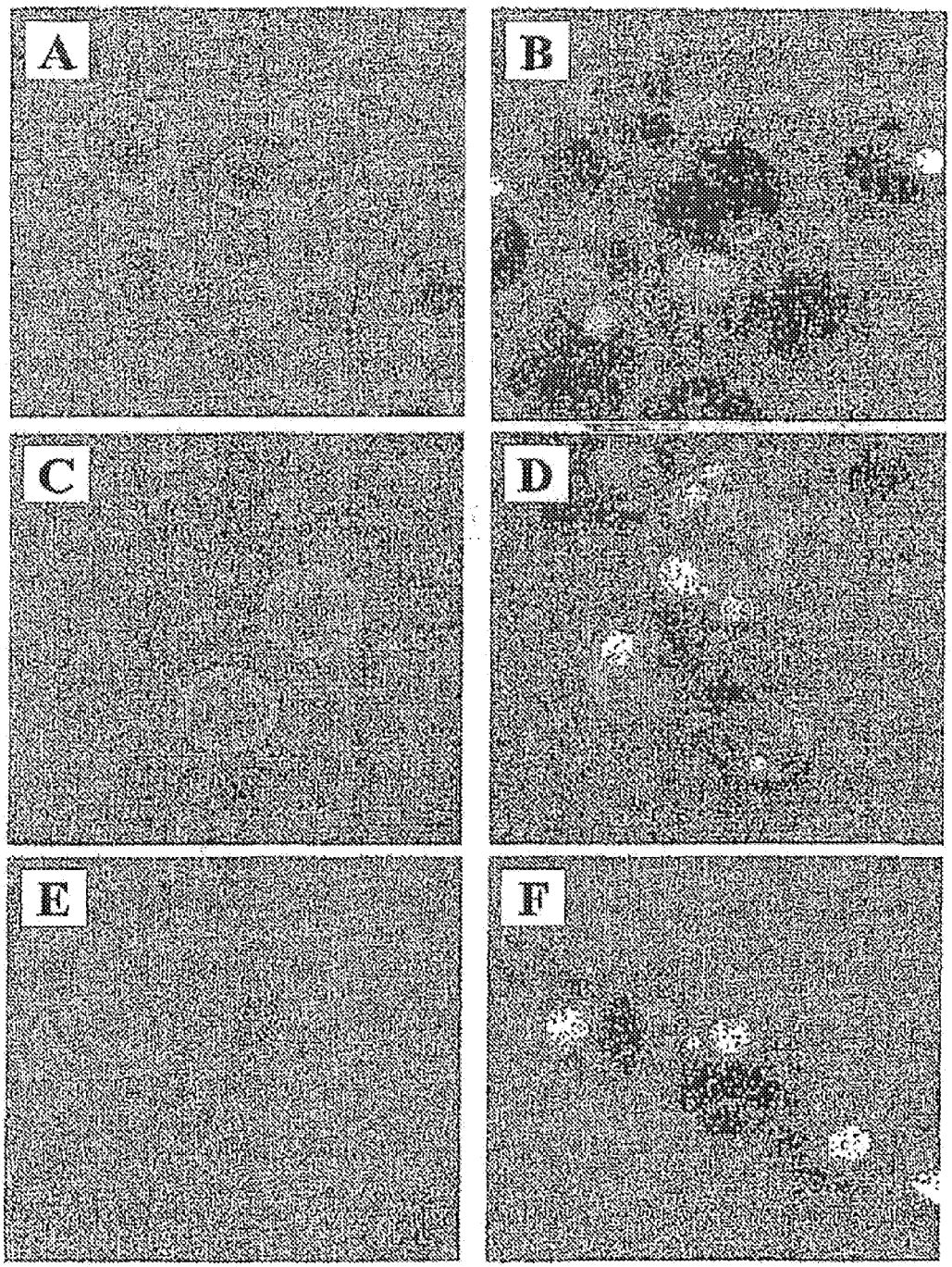
FIG. 5. Confocal micrographs of the dextran-bodipy uptake by PLGA microspheres containing either only BSA (A, C, E) or both BSA and MgCO$_3$ (B, D, F) after incubation in PBST at 37° C. for 1 week, The uptake was carried out at 37° C. in 2.5 mg/ml dextran-bodipy solution for 5 (A, B) and 12 h (C, D). After 12 hr uptake, the microspheres were incubated in blank PBST for another 12 h at 37° C. and then observed by LSCM (E, F). Gain was set at 950 (A, B, E, F) or 680 (C, D).
Figure 6:
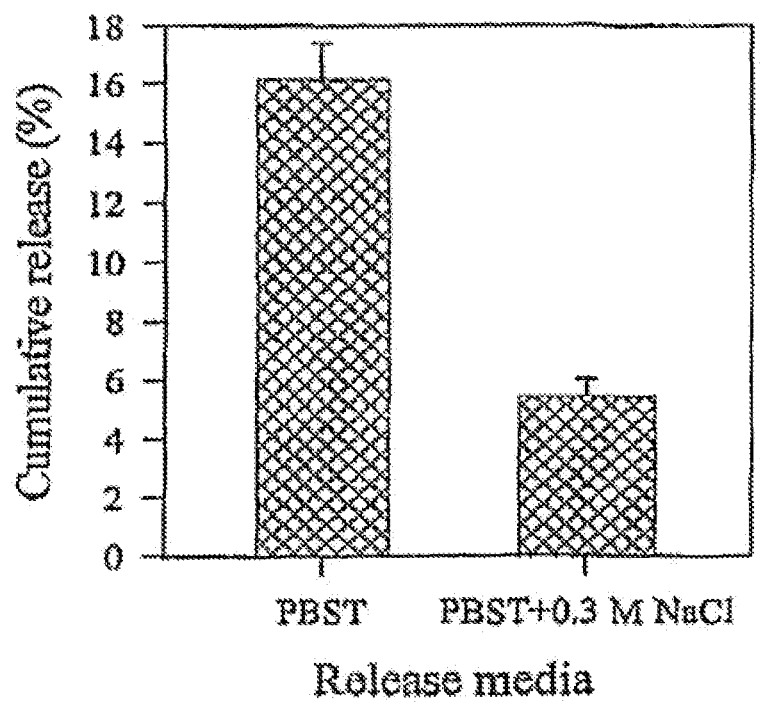
FIG. 6. Effect of release medium on protein release from PLGA microspheres containing 3% MgCO$_3$ after 1-week of incubation at 37° C. (Average±S.T.D., n=3)

More and more evidence suggests that there is an acidic microenvironment in PLGA microspheres causing protein instability. We have used insoluble base, such as $MgCO_3$ as a neutralizing reagent to counteract this harmful condition. However, the effect of insoluble base on important microsphere properties, such as pore state is not clear. To observe the effect of neutralizing insoluble base on pore state in PLGA microspheres, two PLGA microspheres were prepared. Preparation B contained only BSA, a model protein; preparation C contained both protein and 3% $MgCO_3$, as described in Table 1. BSA only and base-containing microspheres showed similar morphology, having numerous small pores in the interior. However, when incubated at 37° C., base-containing microspheres exhibited distinct morphology from that of BSA only microspheres. BSA only microspheres essentially maintained the pore state over 9 days of incubation. On the contrary, base-containing microspheres exhibited significantly altered morphology. Small pores that existed before incubation collapsed into big pores. At 42 days, the shape of BSA only microspheres remained intact while significant amount of base-containing microspheres were fractured and broken. Base-containing microspheres also exhibited different dextran-uptake property. As seen in FIG. 5, when incubated at 37° C. for 1 week, base-containing microspheres had significant dextran uptake, while dextran uptake of BSA-only microspheres was only minimum. After uptake, washing base-containing microspheres for same period of time as uptake period decreased the dextran in microspheres, but substantial amount of dextran remained in the microspheres. The greater uptake of dextran by base-containing microspheres at 1 week suggested a better pore connectivity, which was in accordance with the faster release of BSA from microspheres at that time. Because base decreases polymer erosion rate by neutralization of acidic microenvironment, the greater pore connectivity and the formation of bigger pores from small pores could not be caused by polymer erosion. We suspected that this was caused by the osmotic pressure building up in PLGA microspheres by salt, which was produced by the neutralization of water-soluble acidic polymer degradation products by insoluble base. To test this hypothesis, we compared the protein release rate from base-containing BSA microspheres in PBST and PBST+0.3 M NaCl. If osmotic pressure was responsible for the altered pore structure, we would expect the protein release in 0.3 M+PBST would be much slower than that in PBST because osmotic pressure would be suppressed by the high concentration of salt added in the release medium. As shown in FIG. 6, protein release rate was indeed slower in PBST+0.3 M NaCl than in PBST alone. When incubated in PBST with high concentration of NaCl, base-containing PLGA microspheres showed a dense cross-section in contrast to the porous interior when incubated in PBST with low concentration of NaCl.

Discussions

Methodologies Used in Characterization of Pore State in Biodegradable Microspheres We used three techniques to characterize the pore transition in biodegradable microspheres: 1). Release of both BSA and dextran from same microspheres at different temperatures; 2). Observation of pore state on the surface and in the interior of microspheres by SEM before and after incubation at different temperatures. 3). Investigation of dextran uptake by LSCM with or without pre-incubation at different temperatures. The results from these characterizations formed a panorama of pore transition in and protein release from biodegradable microspheres.

LSCM was previously used to observe the drug distribution and uptake in PLGA microspheres. However, the results of observation were often compromised because pH-sensitive fluorescent probes, such as fluorescein were used. Evidence from different labs and by variety of methods indicates that acidic microenvironment exists in PLGA microspheres. The fluorescence of pH-sensitive probes would be altered in the acidic microenvironment. For example, we found that fluorescein could be completely quenched by acidic pH in some PLGA microspheres (Data not shown). To avoid the potential artifact caused by the pH-sensitive probes in the heterogeneous microenvironment in PLGA microspheres, we used two pH-insensitive probes, bodipy and coumarin, to observe the uptake and distribution of dextran in PLGA microspheres. For PLGA-Glu microspheres, dextran-coumarin was used to avoid the interference of dextran-FITC, which was encapsulated in PLGA-Glu microspheres to characterize dextran release.

Both BSA and probe-conjugated dextran were encapsulated in PLGA-Glu microspheres. Co-encapsulation of small amount of dextran in microspheres enabled us to avoid drawing drug-specific conclusions. It was observed that different protein molecules have different protein-release characteristics, which was attributed to the interaction between polymers and proteins. Because dextran, a highly hydrophilic macromolecules which will unlikely interact with PLGA, exhibited the same release profiles as BSA, at different temperatures, it is reasonable to regard the release at different temperatures a general characteristic of the polymer system.

Implications of Pore Closing in Biodegradable Microspheres on Protein Release

Hydrophilic macromolecules, such as proteins, can only diffuse through pores/channels in PLGA microspheres. Understanding the pore transition in PLGA microspheres is the key to understand how protein drugs were released and to design ideal formulations and microencapsulation process. Common characterization methods to understand the drug release mechanism include water uptake, polymer degradation, polymer erosion rate and the effect of excipients etc. While these characteristics are helpful to understand the release mechanism in some aspects, detailed picture of drug release, cannot be drawn from. Only until recently, were the implications of pore structure change on protein release from PLGA microspheres largely ignored. It has been found that both the external and internal morphology of PLGA microspheres changed substantially during release of peptides over the first 24 h when incubated at pH 4 buffer at 37° C. A non-porous film formed spontaneously at the surface of PLGA microspheres in place of an initially porous surface, which was correlated with a sharp decline in permeability and the cessation of the initial burst. Yamaguchi found that addition of glycerol, which reduced the Tg of the polymer could suppress the initial burst release. The author attributed this to polymer annealing process. Wright used solvent and heating to anneal the pores on the surface of PLGA microspheres in order to reduce the initial burst.

To further characterize the morphology change in PLGA microspheres and understand the mechanism behind this phenomenon, microspheres were incubated at different temperatures. First, it was found that the pores on the surface of the microspheres closed rapidly after immersion in release medium at 37° C., without any plasticizers added. The pore closing was correlated with the slower dextran uptake. Wang based the observation of pore closing on the incubation in pH 4 buffer and found that the pore change at pH 7 buffer was much slower. The observation of rapid pore closing at physiological pH suggested that pore closing on the surface of PLGA microspheres was not a pH-dependent phenomenon. Instead, the rate of pore-closing likely depends on the properties of polymers.

Secondly, we found that pore closing did not happen or only happened very slowly at low temperatures, such as 4° C. and 25° C. This suggests that polymer molecules have to possess certain flexibility for pore closing. This may be related to the Tg of the hydrated polymers. Although both PLGA and PLGA-Glu have a Tg well above 37° C., it is found that, on hydration, the Tg of PLGA polymers dropped below 37° C.

Another interesting finding was that although pore closing wasn't observable inside microspheres at 4° C., dextran uptake experiment suggested that some open pores in PLGA microspheres became isolated during incubation. Some of the dextran absorbed by PLGA microspheres couldn't be released when incubated in blank release medium at the same temperature. This suggested that although the macro-pores remained the same when incubated at 4° C., some of the nano-pores or channels connecting macro-pores, which couldn't be observed by SPM, were closed, leading to that the previously open pores became isolated. Because hydrophilic macromolecules can't diffuse thorough polymer phase, the existing and transition of these connecting nano-pores/channels are important to protein release from PLGA microspheres.

Implications of Pore Opening in Biodegradable Microspheres on Protein Release

Protein release from biodegradable delivery systems usually demonstrates a tri-phasic release curve. The first phase is the release of protein on the surface or having access to the surface through other pores/channels, followed by a no-release or slow-release phase. The third phase is attributed to the polymer erosion. Erosion makes microspheres more porous; protein molecules previously inaccessible to the surface become accessible through pores/channels and will release continuously. However, our results suggested that erosion may not be the solely force to open the previously isolated pores. Osmotic pressure seems the primary driving force to open the previously isolated pores in base-containing microspheres.

It is interesting to find that while previously isolated pores can become open presumably by osmotic pressure-induced polymer rupture, these open pores can become isolated again. It was observed that some of the open pores, to which dextran diffused in during uptake experiment, became isolated; thus a fraction of previously adsorbed dextran were trapped in the microspheres. This suggests that there was a dynamic transition between open pores and isolated pores in PLGA microspheres.

Dynamic Transition Between Open Pores and Isolated Pores in Biodegradable Polymers Base on the above findings, we propose that the pore transition between isolated pores and open pores is the most important phenomenon behind the release of protein drugs from biodegradable polymer microspheres. It was observed that protein molecules were evenly distributed throughout the PLGA microspheres prepared by emulsion-solvent evaporation microencapsulation. While all protein molecules inhabit in pores, only some of the pores are open pores. Once in contact with aqueous medium, water will penetrate rapidly into the polymer matrix and dissolve any soluble protein and excipients. All the protein in open pores will be released rapidly. Because of the meta-stable state of the dried microspheres, pores on the surface of the microspheres and those connecting nano-pores/channels inside microspheres can be rapidly closed depending on polymer properties, which will decrease the release rate, and in many cases, completely stop the release. On the other hand, because of the polymer degradation, the mechanic strength of polymer membranes, which form the walls of pores, is decreasing. The dissolving of proteins, excipients and polymer degradation products is also causing the increase of osmotic pressure in pores. The decreased polymer mechanic strength and increased osmotic pressure cause polymer rupture, so that previously isolated pores become open and previously un-releasable protein molecules released. The pore opening and closing is in a dynamic transition, which dictates the release rate of the protein from polymer. Because the small size and thus the short diffusion distance of microspheres (1-100 µm), even with the high tortuosity the release of proteins would be rapid once it is in open pores. Therefore, the release of drug from PLGA microspheres is primarily controlled by the states of pores and can be regarded as by a "quantum style". The macroscopically observed continuous release profile consists of numerous pulsatile releases of protein from open pores. The nano-pores connecting macro-pores in microspheres play a critical role determining whether a pore is open or isolated, which, however, may not observable by SEM.

Conclusions

The dynamic transition between isolated pores and open pores is the most important phenomenon behind the release of protein drugs from PLGA biodegradable microspheres. The pore closing phenomenon, especially those on the surface of PLGA microspheres can be explained by the meta-stable state of polymer, can be rationalized by thermodynamic and kinetic relations of phase separation process. The isolated pores can be opened, in the case of base-containing microspheres, by osmotic pressure-induced polymer rupture. There existed nano-pores in PLGA microspheres, although not observable by SEM, playing important roles determining the accessibility of macro-pores in microspheres and consequently the protein release profile.

EXAMPLES

Preparation of 1*, 2*, 3*, 4*, 5*, 6*, 7*, 8*, 9*

150 µl of inner water phase (differing glucose concentrations, see Table 3) added to 2 ml of polymer (PLGA-glucose 50/50; average MW=50 kDa) solution in $CH_2Cl_2$ (different polymer concentrations, see Table 3), then homogenized for 1 min at 10,000 RPM in an ice water bath. 2 ml of 0.5% PVA solution (9-10 k, 80% hydrolyzed) added to emulsion and vortexed for 15 seconds. Resulting w/o/w emulsion was immediately poured into 100 ml of 0.5% PVA and stirred for 3 hours.

TABLE 3

PLGA-glu (50:50, 0.31 DL/g) microspheres

| Label | Polymer Concentration (mg/ml) | Glucose Concentration in Inner Water Phase (w/w)% (i.w. phase = 150 µl) | DP/CP (%) (O/$W_2$) |
|---|---|---|---|
| 1* | 200 | 0.0 | 2 |
| 2* |  | 0.2 | 2 |
| 3* |  | 1.0 | 2 |
| 4* | 300 | 0.0 | 2 |
| 5* |  | 0.2 | 2 |
| 6* |  | 1.0 | 2 |
| 7* | 300 | 0.0 | 1 |
| 8* |  | 0.2 | 1 |
| 9* |  | 1.0 | 1 |

After 3 hours, microspheres were washed extensively with $ddH_2O$ and were passed through sieves collecting all microspheres between 20 µm and 90 µm. Microspheres were freeze dried and stored in freezer.

Loading of 1*, 2*, 3*, 4*, 5*, 6*, 7*, 8*, 9*

A solution of bovine serum albumin in PBS buffer (1×, pH 7.4) was created (300 mg BSA/ml).

Approximately 100 mg of microspheres placed into microcentrifuge tubes with 1.0 ml of refrigerated BSA solution and placed on shaker at 4° C. for 3 days. Tubes were inverted at different times over that time period, with the microspheres dispersed into the solution. Microspheres were then placed into 45° C. incubator for 3 days.

Washing of 1*, 2*, 3*, 4*, 5*, 6*, 7*, 8*, 9*

All formulations were removed from incubator and washed with PBS solution. Approximately 1.2 ml of PBS solution added to microcentrifuge tubes, tubes were then inverted and the bottoms tapped to disperse microspheres. For 4* and 5* microcentrifuge tubes were vortexed briefly as well. Microspheres were collected by centrifugation (0.5 min, 2000 RPM) and supernatant removed. Process was repeated 10 times. The $10^{th}$ time exactly 1.5 ml of PBS buffer was kept for analysis after removal.

Microspheres were then freeze dried overnight.

Loading Assay

Approximately 5 mg of each formulation were removed from tubes for loading determination. These 5 mg were dissolved in acetone, with the protein collected by removing the supernatant after centrifugation (1.5 min, 5000 RPM). This was repeated 5×.

Organic solvent traces were removed with concentrator. Coomassie was used to analyze protein amounts in microcentrifuge tubes. Loading analysis determined (Table 4).

TABLE 4

Loading Analysis

| Unknown # | Avg Abs | Conc. of Assay (ug/ml) | Dilution Factor | Adjusted Conc. (ug/ml) | Amount of Protein (mg) | Amount of Microspheres Assayed (mg) | Ratio Protein (mg)/ Microspheres (mg) | % Loading (Ratio × 100) |
|---|---|---|---|---|---|---|---|---|
| 1* (3x Dilution) | 0.653 | 84 | 3 | 253 | 0.253 | 5.52 | 0.0458 | 4.6 |
| 2* (3x (dilution) | 0.575 | 72 | 3 | 217 | 0.217 | 5.54 | 0.0391 | 3.9 |
| 3* (3x dilution) [EXTRAPOLATED] | 0.861 | 116 | 3 | 349 | 0.349 | 5.94 | 0.0587 | 5.9 |
| 4* (3x dilution) | 0.468 | 56 | 3 | 167 | 0.167 | 5.44 | 0.0307 | 3.1 |
| 5* (3x dilution) | 0.264 | 24 | 3 | 73.1 | 0.073 | 5.21 | 0.0140 | 1.4 |
| 6* (3x dilution) | 0.468 | 56 | 3 | 167 | 0.167 | 5.71 | 0.0293 | 2.9 |
| 7* (3x dilution) | 0.320 | 33 | 3 | 99 | 0.099 | 5.7 | 0.0174 | 1.7 |
| 8* (3x dilution) | 0.389 | 44 | 3 | 131 | 0.131 | 5.17 | 0.0253 | 2.5 |
| 9* (3x dilution) | 0.452 | 53 | 3 | 160 | 0.160 | 5.01 | 0.0319 | 3.2 |

Washing Results

Washing results indicated that there was a high amount of protein in the $10^{th}$ wash relative to the loading amounts in certain formulations (Table 5).

TABLE 5

10th Wash Results

| Unknown # | Avg Abs | Conc. of Assay (ug/ml) | Dilution Factor | Adjusted Conc. (ug/ml) | Amount of Protein (mg) | Amount of Protein in Microspheres (From Assay) | Ratio of Protein in Wash to Protein in Microspheres | % of Protein in 10th Wash Relative to Loading | % Loading (Taken from Table 2) |
|---|---|---|---|---|---|---|---|---|---|
| 1* 10th Wash | 0.476 | 60.4 | 1.0 | 60.4 | 9.1E−02 | 0.25 | 0.36 | 35.9 | 4.6 |
| 2* 10th Wash | 0.547 | 71.1 | 1.0 | 71.1 | 1.1E−01 | 0.22 | 0.49 | 49.2 | 3.9 |
| 3* 10th Wash (3x dilution) | 0.356 | 38.2 | 3.0 | 114.6 | 1.7E−01 | 0.35 | 0.49 | 49.3 | 5.9 |
| 4* 10th Wash | 0.132 | <10 | 1.0 | <10 | — | — | — | — | 3.1 |
| 5* $10^{th}$ Wash | 0.093 | <10 | 1.0 | <10 | — | — | — | — | 1.4 |
| 6* 10th Wash | 0.183 | 16.7 | 1.0 | 16.7 | 2.5E−02 | 0.17 | 0.15 | 15.0 | 2.9 |
| 7* 10th Wash | 0.114 | <10 | 1.0 | <10 | — | — | — | — | 1.7 |
| 8* 10th Wash | 0.192 | 18.0 | 1.0 | 18.0 | 2.7E−02 | 0.13 | 0.21 | 20.7 | 2.5 |
| 9* 10th Wash | 0.201 | 19.4 | 1.0 | 19.4 | 2.9E−02 | 0.16 | 0.18 | 18.2 | 3.2 |

Release Results

Approximately 15 mg of all loaded formulations were put in 37° C. incubator with 0.5 ml of PBST (PBS 1×pH 7.4, 0.02% Tween 80) on shaker for release study. Medium was removed after centrifuging (0.5 min, 2000 RPM) at certain time points and replaced with 0.5 ml of medium. These data show that for all formulations that the burst release is large (>60% in the first 24 h), which is an indicator that the steps involved from freeze-drying to rehydration (i.e., freezing, drying, re-evacuation, and rehydration) may have damaged the polymer in pore-closing regions. Use of the polymer without freeze-drying and rehydration, directly after preparation or after storage at 4° C. is expected to minimize this undesirable effect.

Figure 7:
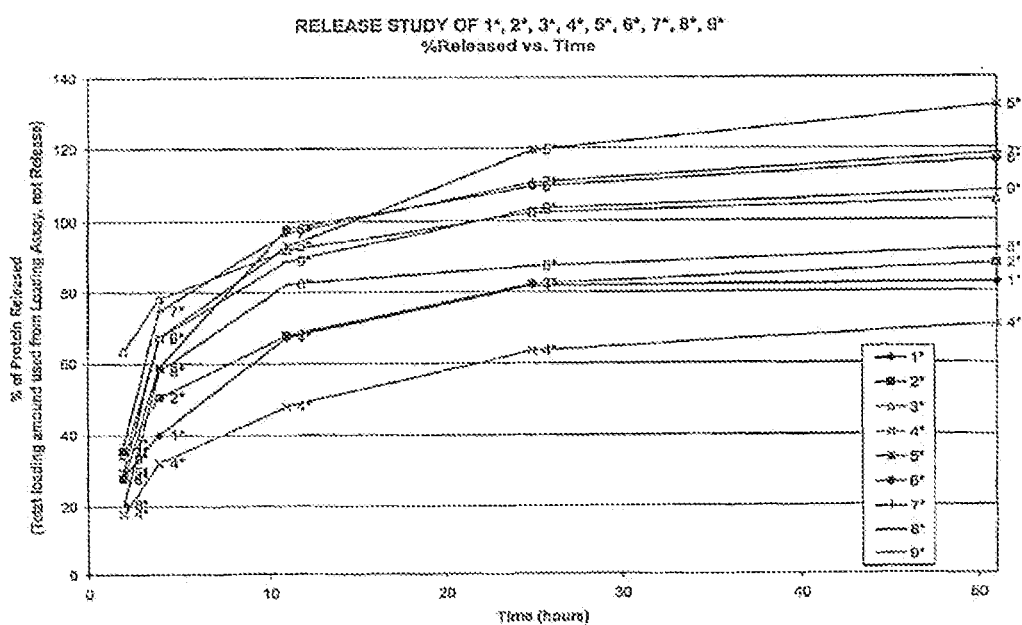
FIG. 7. Release chart drawn showing % of protein released with respect to amount loaded (amount loaded taken from loading assay).

Release chart drawn (FIG. 7) showing % of protein released with respect to amount loaded (amount loaded taken from loading assay).

The examples described herein are for illustrative purposes only and are not meant to limit the invention as set forth in the claims.

The invention claimed is:

1. A method for encapsulating a biomacromolecule in a pore-containing polymer comprising the steps of:
   a. providing an encapsulating solution containing the biomacromolecule and the pore-containing polymer, wherein the pore-containing polymer is insoluble in the encapsulating solution;
   b. contacting the biomacromolecule with the pore-containing polymer for a time sufficient for the biomacromolecule to enter the pores of the pore-containing polymer; and
   c. causing the pores of the pore-containing polymer to close, partially or fully, by:
      elevating the temperature of the encapsulating solution, changing the pH of the encapsulating solution,
incorporating a pore-closing additive in the pore-containing polymer, or
incorporating a pore-closing additive in the encapsulation solution;
wherein the biomacromolecules that had entered the pores in step b are thereby encapsulated in the pore-containing polymer.

2. The method of claim 1 wherein the biomacromolecule is selected from the group consisting of proteins, peptides, poly(nucleic acid) drugs, antigens, and combinations thereof.

3. The method of claim 1 wherein the pore-containing polymer is a preformed microsphere.

4. The method of claim 1 wherein the pore-containing polymer is a preformed tissue engineering scaffold.

5. The method of claim 1 wherein pore-containing polymer is poly(DL-lactide-co-glycolide) (PLGA).

6. The method of claim 2 wherein the pore-containing polymer is a pre-formed microsphere.

7. The method of claim 6 wherein the preformed microsphere is a poly(DL-lactide-co-glycolide) (PLGA) microsphere.

8. The method of claim 7 wherein the pores are caused to be closed, partially or fully by elevating the temperature of the encapsulating solution.

9. The method of claim 7 wherein the pores are caused to be closed, partially or fully by changing the pH of the encapsulating solution.

10. The method of claim 7 wherein the pores are caused to be closed, partially or fully by incorporating a pore-closing additive in the pore-containing polymer.

11. The method of claim 2 wherein the pore-containing polymer is a preformed tissue engineering scaffold.

12. The method of claim 11 wherein the preformed tissue engineering scaffold comprises PLGA.

13. The method of claim 11 wherein the pores are caused to be closed, partially or fully by elevating the temperature of the encapsulating solution.

14. The method of claim 11 wherein the pores are caused to be closed, partially or fully by changing the pH of the encapsulating solution.

15. The method of claim 11 wherein the pores are caused to be closed, partially or fully by incorporating a pore-closing additive in the pore-containing polymer.

16. A method for encapsulating a molecule in a pore-containing polymer comprising the steps of:
a. providing an encapsulating solution containing the molecule and the pore-containing polymer, wherein the pore-containing polymer is insoluble in the encapsulating solution;
b. contacting the molecule with the pore-containing polymer for a time sufficient for the molecule to enter a pore of the pore-containing polymer; and
c. causing the pore of the pore-containing polymer to close, partially or fully, by:
elevating the temperature of the encapsulating solution,
changing the pH of the encapsulating solution,
incorporating a pore-closing additive in the pore-containing polymer, or
incorporating a pore-closing additive in the encapsulation solution;
wherein the molecule that had entered the pore in step b is thereby encapsulated in the pore-containing polymer.

17. A pore-containing polymer encapsulating a biomacromolecule made according to the method of claim 1.

18. A pore-containing polymer encapsulating a molecule made according to the method of claim 16.

* * * * *

UNITED STATES PATENT AND TRADEMARK OFFICE
CERTIFICATE OF CORRECTION

PATENT NO. : 8,017,155 B2
APPLICATION NO. : 11/596524
DATED : September 13, 2011
INVENTOR(S) : Steven P. Schwendeman et al.

It is certified that error appears in the above-identified patent and that said Letters Patent is hereby corrected as shown below:

Column 2, line 55, "is" should be --are--.

Column 3, line 1, "embodiment" should be --embodiments--.

Column 3, line 14, after "using" delete "of".

Column 3, line 16, after "using" delete "of".

Column 3, line 26, after "n=3)" insert --.--.

Column 3, line 29, after "n=3)" insert --.--.

Column 3, line 32, after "(lines)" insert --.--.

Column 3, line 35, after "(lines)" insert --.--.

Column 3, line 39, "1 week," should be --1 week.--.

Column 5, line 48, "polymers" should be --Polymers--.

Column 6, line 3, "cool" should be --cooled--.

Column 6, line 7, "laboratory" should be --Laboratory--.

Column 6, line 32, "$133 \times 10^{-}3$" should be --$133 \times 10^{-3}$--.

Column 6, line 49, "condition" should be --conditions--.

Column 6, lines 63, "chromatography," should be --chromatography.--.

Column 7, line 17, "In Vitro" should be --In vitro--.

Column 7, line 36, "(Car Zeiss" should be --(Carl Zeiss--.

Column 8, line 6, "engineering" should be --Engineering--.

Column 8, line 17, "a encapsulation" should be --an encapsulation--.

Column 8, line 20, "a encapsulation" should be --an encapsulation--.

Column 9, line 21, "release," should be --release.--.

Column 9, line 23, delete "degree".

Column 10, line 59, "L SCM" should be --LSCM--.

Signed and Sealed this
Sixth Day of March, 2012

David J. Kappos
*Director of the United States Patent and Trademark Office*

CERTIFICATE OF CORRECTION (continued)
U.S. Pat. No. 8,017,155 B2

Column 14, line 35, "thorough" should be --through--.

Column 14, line 50, "solely" should be --sole--.

Column 14, line 66, "Base" should be --Based--.

Column 15, line 38, after "not" insert --be--.

Column 19, line 16, Claim 5, after "wherein" insert --the--.